US010194834B2

(12) United States Patent
Selvaraj et al.

(10) Patent No.: US 10,194,834 B2
(45) Date of Patent: Feb. 5, 2019

(54) DETECTION OF SLEEP APNEA USING RESPIRATORY SIGNALS

(71) Applicant: Vital Connect, Inc., Campbell, CA (US)

(72) Inventors: Nandakumar Selvaraj, Santa Clara, CA (US); Ravi Narasimhan, Sunnyvale, CA (US)

(73) Assignee: VITAL CONNECT, INC., San Jose, CA (US)

( * ) Notice: Subject to any disclaimer, the term of this patent is extended or adjusted under 35 U.S.C. 154(b) by 459 days.

(21) Appl. No.: 14/156,370

(22) Filed: Jan. 15, 2014

(65) Prior Publication Data

US 2014/0200474 A1    Jul. 17, 2014

Related U.S. Application Data

(60) Provisional application No. 61/753,277, filed on Jan. 16, 2013.

(51) Int. Cl.
*A61B 5/08* (2006.01)
*A61B 5/087* (2006.01)
(Continued)

(52) U.S. Cl.
CPC .......... *A61B 5/0826* (2013.01); *A61B 5/0806* (2013.01); *A61B 5/087* (2013.01);
(Continued)

(58) Field of Classification Search
None
See application file for complete search history.

(56) References Cited

U.S. PATENT DOCUMENTS 6,527,729 B1 *   3/2003   Turcott ............... A61B 5/0002
                                                      600/528
6,881,192 B1 *   4/2005   Park .................. A61N 1/36585
                                                      600/484
(Continued)

FOREIGN PATENT DOCUMENTS

JP        2005160644 A       6/2005
JP        2007504917 A       3/2007
(Continued)

OTHER PUBLICATIONS

The International Search Report and the Written Opinion of the International Searching Authority issued for International application No. PCT/US2014/011913, dated May 2, 2014.
(Continued)

*Primary Examiner* — Michael R Bloch
(74) *Attorney, Agent, or Firm* — Brundidge & Stanger, P.C.

(57) ABSTRACT

A method and system for sleep apnea detection are disclosed. The method comprises detecting at least one respiratory signal and utilizing a detection algorithm to automatically detect at least one sleep apnea event from the at least one respiratory signal. The system includes a sensor to determine at least one respiratory signal, a processor coupled to the sensor, and a memory device coupled to the processor, wherein the memory device includes a detection algorithm and an application that, when executed by the processor, causes the processor to utilize the detection algorithm to automatically determine at least one sleep apnea event from the at least one respiratory signal.

8 Claims, 5 Drawing Sheets

(51) Int. Cl.
*A61B 5/00* (2006.01)
*A61B 5/0402* (2006.01)

(52) U.S. Cl.
CPC .......... *A61B 5/4818* (2013.01); *A61B 5/7203* (2013.01); *A61B 5/7207* (2013.01); *A61B 5/0402* (2013.01); *A61B 5/0878* (2013.01)

(56) References Cited

U.S. PATENT DOCUMENTS

| | | | |
|---|---|---|---|
| 7,942,822 B1 | 5/2011 | Koh | |
| 8,740,808 B2 | 6/2014 | Curti et al. | |
| 2002/0029000 A1 | 3/2002 | Ohsaki et al. | |
| 2002/0082510 A1* | 6/2002 | Toole | A61B 5/04011 600/512 |
| 2002/0169384 A1* | 11/2002 | Kowallik | A61M 16/0051 600/529 |
| 2003/0055348 A1* | 3/2003 | Chazal | A61B 5/04325 600/509 |
| 2003/0114768 A1* | 6/2003 | Fischer | A61B 5/0428 600/509 |
| 2003/0130589 A1* | 7/2003 | Poezevera | A61N 1/3601 600/533 |
| 2007/0032733 A1 | 2/2007 | Burton | |
| 2007/0093724 A1* | 4/2007 | Nakano | A61B 5/087 600/538 |
| 2007/0239057 A1 | 10/2007 | Pu et al. | |
| 2008/0319513 A1 | 12/2008 | Pu et al. | |
| 2009/0203972 A1 | 8/2009 | Heneghan et al. | |
| 2009/0264784 A1* | 10/2009 | Stasz | A61B 5/0816 600/529 |
| 2010/0125310 A1* | 5/2010 | Wilson | A61N 1/3601 607/42 |
| 2010/0217133 A1 | 8/2010 | Nilsen et al. | |
| 2011/0301484 A1* | 12/2011 | Curti | A61B 5/087 600/537 |
| 2014/0163343 A1 | 6/2014 | Heneghan et al. | |
| 2014/0221849 A1 | 8/2014 | Farringdon et al. | |
| 2014/0221850 A1 | 8/2014 | Farringdon et al. | |

FOREIGN PATENT DOCUMENTS

| | | |
|---|---|---|
| JP | 2007105117 A | 4/2007 |
| JP | 2007517553 A | 7/2007 |
| JP | 2009538720 A | 11/2009 |
| JP | 2010540124 A | 12/2010 |
| JP | 2011522618 A | 8/2011 |
| WO | 2011143631 A2 | 11/2011 |

OTHER PUBLICATIONS

Japanese Office Action (Notice of Reasons for Rejection) dated Aug. 9, 2016.
S. Nandakumar et al "Detection of Sleep Apnea on a Per-second basis using Respiratory Signals", The Effect of Applied Compressive Loading on Tissue-Engineered Cartilage Constructs Cultured with TGF-BETA3, IEEE, Jul. 3, 2013, pp. 2124-2127.
Extended European Search Report (EESR) dated Sep. 12, 2016.

\* cited by examiner

DETECTION OF SLEEP APNEA USING RESPIRATORY SIGNALS

CROSS-REFERENCE TO RELATED APPLICATION

This application claims benefit under 35 USC 119(e) of U.S. Provisional Patent Application No. 61/753,277, filed on Jan. 16, 2013, entitled "WIRELESS REMOTE MONITORING OF VITAL SIGNS, ACTIVITY AND SLEEP," which is incorporated herein by reference in its entirety.

FIELD OF THE INVENTION

The present invention relates to wireless sensor devices, and more particularly, to detecting sleep apnea via respiratory signals using the wireless sensor devices.

BACKGROUND

The accurate measurement of sleep related diseases such as sleep apnea is important to managing the overall health of a person. Sleep Apnea Syndrome (SAS) is a major sleep disorder that causes recurrent episodes of complete (apnea) or partial (hypopnea) blockage of the upper airway during sleep. One of the metrics that quantify the severity of SAS is the Apnea-Hypopnea Index (AHI) index, which is the number of apnea and hypopnea events per hour (EPH) averaged over the duration of sleep. The prevalence of SAS is approximately 3 to 7% in adult men and 2 to 5% in adult women and the disease prevalence in higher in different population subsets such as the obese or older groups. Additionally, there is a large proportion of undiagnosed SAS patients because routine clinical visits and blood tests usually do not detect SAS. Accurate and timely SAS diagnosis is important because there are adverse health consequences of this disorder, including daytime hypersomnolence, neurocognitive dysfunction, cardiovascular disease, metabolic dysfunction and respiratory failure.

Conventional sleep testing and sleep staging of a person is done via cumbersome clinical studies and in-center testing facilities. A polysomnography (PSG) test is the gold standard test for the diagnosis of SAS. The PSG test involves the monitoring during overnight sleep of multiple physiological signals including electroencephalography (EEG), airflow, thoracic/chest or abdominal respiratory inductive plethysomography (RIP) effort signals, and oxygen saturation. The PSG test conducted at a sleep center facility is obtrusive and uncomfortable because they require an abundance of sensors and interfere with the person's sleep and prevent a representative sample of sleep from being obtained. The PSG test also involves high operating costs, in part because of the dedicated equipment, facilities, and personnel required to conduct the test. Additionally, the PSG test is time consuming and often varies based on the subjective interpretation of medical experts.

Therefore, there is a strong need for a solution that overcomes the aforementioned issues. The present invention addresses such a need.

SUMMARY

A method and system for sleep apnea detection are disclosed. In a first aspect, the method comprises detecting at least one respiratory signal and utilizing a detection algorithm to automatically detect at least one sleep apnea event from the at least one respiratory signal.

In a second aspect, the system includes a sensor to determine at least one respiratory signal, a processor coupled to the sensor, and a memory device coupled to the processor, wherein the memory device includes a detection algorithm and an application that, when executed by the processor, causes the processor to utilize the detection algorithm to automatically determine at least one sleep apnea event from the at least one respiratory signal.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
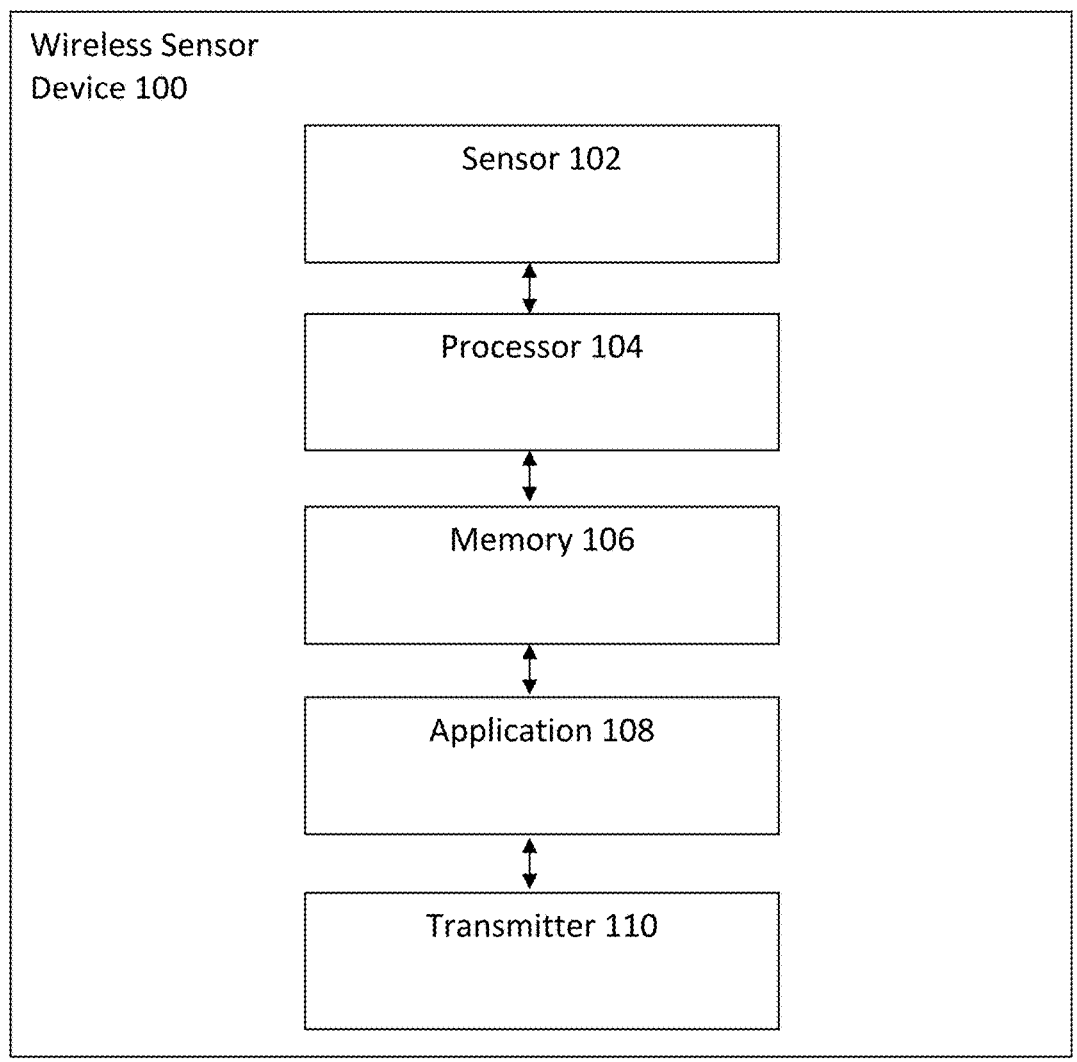
FIG. 1 illustrates a wireless sensor device for automated sleep apnea detection using respiratory signals in accordance with an embodiment.

The present invention relates to wireless sensor devices, and more particularly, to detecting sleep apnea via respiratory signals using the wireless sensor devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Certain portable Sleep Apnea Syndrome (SAS) monitor devices are utilized to diagnose SAS including but not limited to respiratory and effort sensors such as Type-4 monitors that utilize at least one channel including but not limited to oxygen saturation or airflow. Respiratory and effort sensors alone are not accurate for SAS diagnosis because they analyze the physiological signals with poor time resolution ranging from 15 seconds to a few minutes. Such large temporal windows extend detected apnea/hypopnea events in a single segment to many segments and therefore result in false positive events and an overestimation of AHI values.

Wireless and wearable sensor portable devices are used to accurately detect a variety of health related concerns including sleep related diseases such as SAS. By utilizing a wireless sensor device and integrated algorithms that classify apnea events with a fine time resolution, the testing and accurate diagnosis of SAS is achieved out-of-center and in a more comfortable setting for the patient.

A method and system in accordance with the present invention provides a wireless sensor device that is in patch form factor is attached to a user to automatically and continuously detect a variety of health related and physiological signals including but not limited to nasal airflow respiration (NAR) signals. The wireless sensor device then utilizes an integrated apnea detection algorithm to extract features based on filtering and statistical dispersion of the NAR signals and to detect apnea and hypopnea events on a real-time or per-second basis. The apnea detection algorithm is applicable to other types of respiratory signals including but not limited to RIP effort signals. Inclusion of additional channels including but not limited to oxygen desaturation and respiratory effort based on RIP increases the ability to discriminate between apnea and hypopnea events as well as types of apnea events.

The apnea detection algorithm is optimized according to the product of sensitivity and positive predictive values of apnea events among a training dataset of a predetermined number of apnea subjects including but not limited to 50 individuals with a constraint on a false positive rate among a training dataset of a predetermined number of control subjects including but not limited to 50 control individuals. In another embodiment, hypopnea detection is incorporated into the wireless sensor to enhance the performance of the apnea detection algorithm.

FIG. 1 illustrates a wireless sensor device 100 for automated sleep apnea detection using respiratory signals in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached to a user to detect various physiological signals including but not limited to nasal airflow respiration (NAR) signals via the sensor 102. The sensor 102 obtains data from the user which is transmitted to the memory 106 and in turn to the application 108 via the processor 104. The processor 104 executes the application 108 to process and obtain information regarding the user's health. The information is transmitted to the transmitter 110 and in turn relayed to another user or device for further analysis and storage. In another embodiment, the transmitter 110 transmits the various detected physiological signals in raw form to a remote server for processing, analysis, and storage.

In one embodiment, the sensor 102 is any of a microelectromechanical system (MEMS) tri-axial accelerometer and an embedded sensor with electrodes and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention. Additionally, one of ordinary skill in the art readily recognizes that a variety of wireless sensor devices can be utilized including but not limited to wearable sensors, a wireless sensor device in a patch form-factor, tri-axial accelerometers, uni-axial accelerometers, bi-axial accelerometers, gyroscopes, and pressure sensors and that would be within the spirit and scope of the present invention.

To describe the features of the present invention in more detail, refer now to the following description in conjunction with the accompanying Figures.

The Sleep Heart Health Study (SHHS) is a prospective cohort first study held during 1995-1998 to investigate SAS and other sleep-disordered breathing as risk factors for the development of cardiovascular disease. In the first study, 6441 individuals aged 40 years or older and not being treated for sleep apnea were recruited to undergo an overnight home PSG, create a first PSG database, complete several questionnaires, and undergo physical examination. A second PSG database (SHHS-2) was obtained from 3295 individuals during 2001-2003 in a second study.

In one embodiment, the records and data of the SHHS-2 PSG database are utilized to create the training datasets for both a group of sleep apnea subjects (e.g. patients that suffer from sleep apnea) and a group of control subjects (e.g. patients that do not suffer from sleep apnea). In another embodiment, a plurality of other PSG databases are created from other sets and examinations of patients and the plurality of other PSG databases are then utilized to create the training datasets for both the group of sleep apnea subjects and the group of control subjects.

In one embodiment, a predetermined number (e.g. 100) of PSG records are randomly selected from any of the first PSG database, the second PSG database, and the plurality of other PSG databases for both the group of sleep apnea subjects (AHI values of 30 to 75) and for the group of control subjects (AHA values<5). Furthermore, training and testing datasets (each with a sample size n=100) are randomly selected to represent 50 subject control data and 50 subject apnea data in each of the training and testing datasets. In any of the first PSG database, the second PSG database, and the plurality of other PSG databases, the NAR signals are sampled at a predetermined level (e.g. 10 Hz) and are generated using a device including but not limited to an oral-nasal thermocouple.

In one embodiment, a wireless sensor device in accordance with the present invention utilizes an apnea detection algorithm that is based on the NAR signals generated for the first PSG database and the second PSG databases. In another embodiment, a wireless sensor device in accordance with the present invention utilizes an apnea detection algorithm that is based on the NAR signals generated for the plurality of other PSG databases.

In any of the PSG databases (e.g. first, second, plurality of other), respiratory event annotations are recorded including but not limited to apnea and hypopnea event start times and durations. Apnea events are identified if a peak-to-trough amplitude of the NAR signals is less than 25% of an amplitude of a preceding baseline period (with regular breathing and stable oxygen levels) for at least a predetermined time period (e.g. 10 seconds). Hypopnea events are identified if an amplitude of any respiratory signal decreases below 70% of an amplitude of the preceding baseline period for at least a predetermined time period (e.g. 10 seconds) and for at least a number of breaths (e.g. 2 breaths). The apnea events are further identified as any of "obstructive", "central", and "mixed" based on whether the effort to breathe, observed as a displacement in either chest abdominal respiratory inductive plethysomography (RIP) or abdominal RIP signals, is present during the apnea events.

In one embodiment, the apnea detection algorithm is designed to detect apnea events based on features extracted from the NAR signals. In another embodiment, the apnea detection algorithm is designed to detect apnea and hypopnea events based on features extracted from the NAR signals and can distinguish between the types of apnea (e.g. obstructive, central, mixed).

Figure 2:
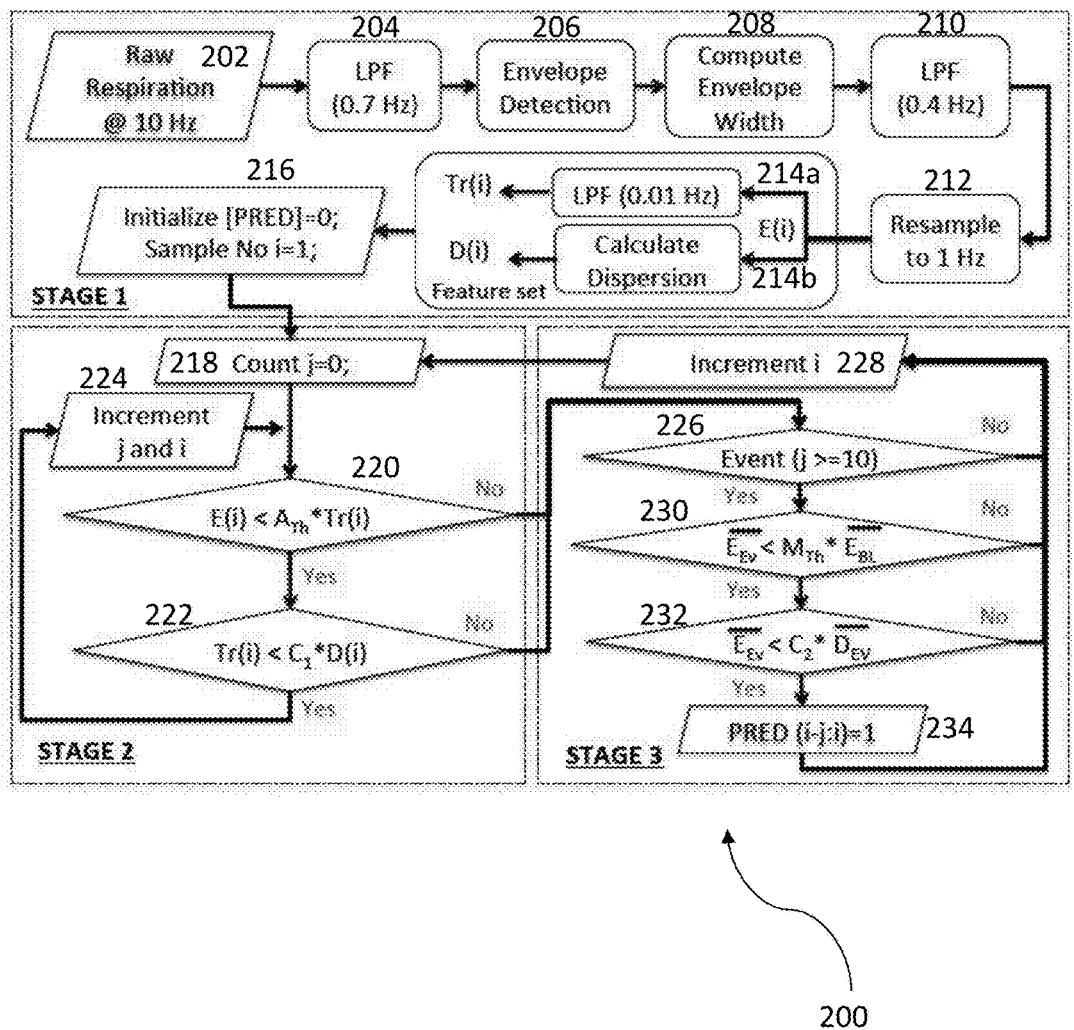
FIG. 2 illustrates an apnea detection algorithm utilized by a wireless sensor device in accordance with an embodiment.

FIG. 2 illustrates an apnea detection algorithm 200 utilized by a wireless sensor device in accordance with an embodiment. The apnea detection algorithm 200 consists of three distinct stages: stage 1 for preprocessing and feature extraction, stage 2 for candidate event detection, and stage 3 for false positive reduction and confirmation of an apnea event detection. In one embodiment, the stage 1 preprocessing is conducted by filtering a respiratory signal with a $4^{th}$-order elliptic filter and the features extracted include but are not limited to lowpass (e.g. 0.4 Hz) filtered envelope width, very low frequency (e.g. 0.01 Hz) trend of the envelope width, and statistical dispersion of the envelope width as a difference between a range of percentiles including but not limited to the $90^{th}$ and $10^{th}$ percentiles over a predetermined time window (e.g. 120 seconds).

The wireless sensor device is attached to a user (e.g. near the chest area) and automatically and continuously detects raw respiratory signals including but not limited to nasal airflow respiratory (NAR) signals, via step 202. At least one of the raw NAR signals is low-pass filtered (LPF) at a predetermined passband corner frequency (fc), via step 204. The predetermined fc includes but is not limited to 0.7 Hz which represents the normal bandwidth of the NAR signal during sleep.

All local maxima and local minima points of the NAR signal are interpolated using piecewise cubic Hermite interpolation to obtain upper and lower envelopes, via step 206. An envelope width signal is calculated from the NAR signal as a difference signal between the upper and low envelopes, via step 208. The envelope width signal reflects changes in instantaneous respiratory amplitudes and is low-pass filtered at a predetermined frequency (e.g. fc=0.4 Hz), via step 210, and then resampled at a predetermined frequency (e.g. 1 Hz) to obtain E(i) as a first feature for the apnea event detection, via step 212. The feature signal E(i) represents a low-pass filtered envelope width that retains variability of the respiratory instantaneous amplitudes up to 0.4 Hz because power beyond 0.4 Hz is negligible.

The signal E(i) is again low-pass filtered at a predetermined frequency (e.g. fc=0.01 Hz) to obtain an adaptive trend mean that exhibits very low frequency variability of respiratory instantaneous amplitudes which is denoted as a second feature $T_r(i)$, via step 214a. The spectrum of the NAR signal exhibits increased power in the range of 0.01 to 0.1 Hz during apnea events. In one embodiment, the three low-pass filters utilized in steps 204, 210, and 214a are $4^{th}$-order elliptic filters with a passband ripple of 0.5 decibel (dB) and a stopband attenuation of 30 dB. In another embodiment, the three low-pass filters are different types of filters with varying decibel values.

In one embodiment, the statistical dispersion of the signal E(i) is calculated as a difference between the $90^{th}$ and $10^{th}$ percentile values for a moving window of a predetermined duration (e.g. 120 seconds) which is denoted as a third feature D(i), via step 214b. The moving window length is chosen to minimize false positive events that may arise from long apnea episodes. The feature D(i) together with the feature $T_r(i)$ detect transitions between normal and apnea episodes.

An event prediction vector [PRED] with a length of a feature vector in seconds is set to be zero, via step 216. Setting [PRED] to zero initializes an initial condition of the event prediction vector to assume the presence of control data (e.g. the presence of data that does not include sleep apnea events), via step 216. Feature signals are analyzed for each sample index i on a per-second basis starting with the sample number of i=1 to identify potential sleep apnea events as follows. A temporary count is initialized to be j=0, via step 218. The apnea detection algorithm block determines whether the following two conditions are satisfied on a per-sample basis to detect a candidate event: 1) an instantaneous amplitude of the NAR signal E(i) is less than an amplitude threshold $A_{Th}$ times the trend mean $T_r(i)$, via step 220, and 2) a transient decrease in E(i) amplitudes during apnea skew its probability distribution and increase a range of its statistical dispersion D(i) such that $T_r(i)$ is less than C1 times D(i), via step 222.

As long as these two conditions are both satisfied on a per-second basis, the count j is incremented, via step 224. When a sample does not satisfy either of these conditions, the count is not updated. The apnea detection algorithm block determines whether or not the current count j is greater than or equal to 10, via step 226. If the current count j is less than 10 (j<10), the count j is reset to 0 and the next sample i (e.g. i+1) is processed, via step 228. If the current count j is greater than or equal to 10 (j>=10), then a candidate event is detected. In one embodiment, the count j threshold is chosen as 10 because a potential event that can last at least for 10 seconds qualifies as an apnea event. The rationale for considering the above two conditions is that the signal E(i) may decrease below the trend mean $T_r(i)$ briefly but may not stay lower for at least 10 seconds during a normal respiratory event. Additionally, the dispersion metric D(i) is typically lower than the trend mean $T_r(i)$ during a normal respiratory event, but an apnea event causes D(i) to increase above $T_r(i)$.

Once a candidate event has been detected that consists of the past j+1 samples, the apnea detection algorithm processed by the wireless sensor device moves into stage 3 and compares two conditions on a pre-event basis with respect to a baseline that refers to a predetermined window consisting of the preceding 10 samples to the candidate event that was just detected. The apnea detection algorithm compares the two conditions to exploit the linear relationships between the features thereby reducing the probability of detecting false positive events.

The first condition that the apnea detection algorithm determines is whether the mean of E(i) for an apnea event (denoted as $E_{Ev}$) is less than $M_{Th}$ times the mean of E(i) during baseline (denoted as $E_{BL}$) where $M_{Th}$ refers to a mean threshold, via step 230. The second condition that the apnea detection algorithm determines is whether $E_{Ev}$ is less than C2 times the mean dispersion metric of the same event (denoted as $D_{Ev}$), via step 232. If both of the conditions described by steps 230 and 232 are satisfied, the candidate event/window is confirmed as an apnea event, via step 234. If either of the conditions described by steps 230 and 232 are not satisfied, the candidate event is not confirmed as an apnea event and thus no apnea event is detected.

In one embodiment, the two conditions described by steps 230 and 232 are utilized because the respiratory signal decreases to less than 25% of the baseline values for at least 10 seconds during an apnea event and so $E_{Ev}$ should be less than 25% of $E_{BL}$. Instead of selecting an arbitrary value of 25% as the mean threshold, the optimal value of $M_{Th}$ is selected from training data utilized by the wireless sensor device and the apnea detection algorithm. Additionally, the difference between $D_{Ev}$ and $E_{Ev}$ is larger for an apnea event than for a hypopnea event and so by optimizing the constant C2, the probability of false positives originating from hypopnea events is reduced. Therefore, the four parameters $A_{Th}$, C1, $M_{Th}$, and C2 are determined to maximize the product of the sensitivity Se (Se=TP/(TP+FN)*100) and the positive predictive value PPV (PPV=TP/(TP+FP)*100) for apnea subjects of the training set where TP, FP, and FN respectively represent true positives, false positives, and false negatives.

In another embodiment, a plurality of users that are utilizing a plurality of wireless sensor devices with embedded apnea detection algorithms have user data transmitted to a centralized database or cloud computer system to enable the various thresholds and optimal values (e.g. optimal value $M_{Th}$) to be continuously updated and optimized and then transmitted back to the wireless sensor device for usage by the apnea detection event.

In one embodiment, after various data is compiled and calculated by the wireless sensor device to create a testing dataset with a predetermined number of testing subjects (e.g. n=100 where 50 are apnea subjects and 50 are control subjects), the testing dataset is transmitted to an another device (e.g. offline system, online system, another computer, cloud computer system, server database) for further analysis and comparison to a training dataset with a predetermined number of training subjects (e.g. n=100 where 50 are apnea subjects and 50 are control subjects).

Three feature signals and reference annotations are initially obtained for the predetermined number of training subjects and stored in the training dataset. Selection of optimal values for the four variables $A_{Th}$, C1, $M_{Th}$, and C2 are carried out in a two step process. First, the four variables are coarsely chosen as arbitrary vectors (0 to 2 with an increment of 0.2) and for every combination of the four variables, the false positive rate ($FPR_C$ in events per hour (EPH)) is obtained for all of the control subjects (e.g. 50) in the training dataset. FPRC is calculated as a total number of detected false positive events over a total number of hours. Additionally, for all of the apnea subjects (e.g. 50) in the training dataset, $Se_A$ (Sensitivity of Apnea Group denoted as a subscript A), $PPV_A$ (Positive Predictive Value of Apnea Group) and $FPR_A$ (False Positive Rate of Apnea Group) are obtained.

Second, a grid search is conducted for each $FPR_C$ between 1 and 4 with an increment of 0.1 (because the target FPR in control subjects should be less than 5, which is an arbitrary threshold that would increase the probability of detecting control subjects) to find the highest probability (product of $Se_A$ and $PPV_A$) of apnea detection. With the identified course values of the four variables, another grid search is conducted by repeating the aforementioned process with fine values of the four variables. Therefore, optimization of the four variables involves a course grid search followed by a fine grid search. During the course grid search, the four variables are incremented by 0.2 and optimal values are obtained that produce the highest probability of apnea detection. Based on the results of the course grid search, new vectors of the four variables are defined with increments of 0.02 and a fine grid search is conducted to identify optimized values.

The performance of the apnea detection algorithm is evaluated using the testing dataset that incorporates the optimized four variables garnered from the training dataset. On a subject by subject basis as well as overall, the $Se_A$ and $PPV_A$ in % and the $FPR_A$ in EPH are calculated from the apnea subjects in the training dataset and $FPR_C$ in EPH is calculated from the control subjects in the training dataset. The values are given in mean+−SE (standard error). In one embodiment, the optimal four parameters/variables for the apnea detection algorithm are $A_{Th}$=1.42, C1=0.8, $M_{Th}$=0.92, and C2=0.22.

Figure 3:
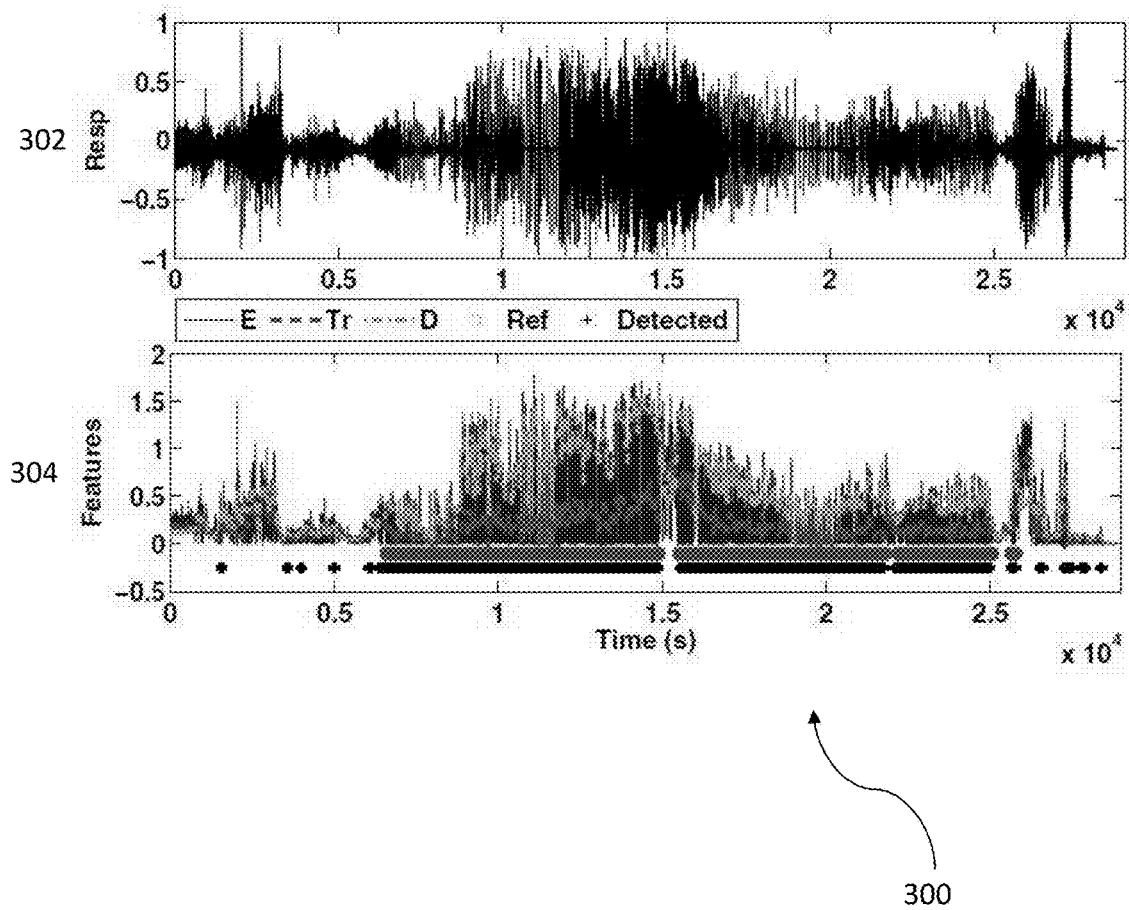
FIG. 3 illustrates a diagram depicting automated sleep apnea detection using respiratory signals in accordance with an embodiment.

FIG. 3 illustrates a diagram 300 depicting automated sleep apnea detection using respiratory signals in accordance with an embodiment. The diagram 300 includes a first graph 302 that depicts a respiratory signal and a second graph 304 that depicts an output of the apnea detection algorithm utilized by a wireless sensor device to automatically detect sleep apnea events using respiratory signals. The second graph 304 denotes derived features E(i), $T_r$(i), and D(i), reference annotations (marked as o), and detected annotations (marked as +) for each second and includes a high sensitivity (98+%) for apnea detection.

Figure 4:
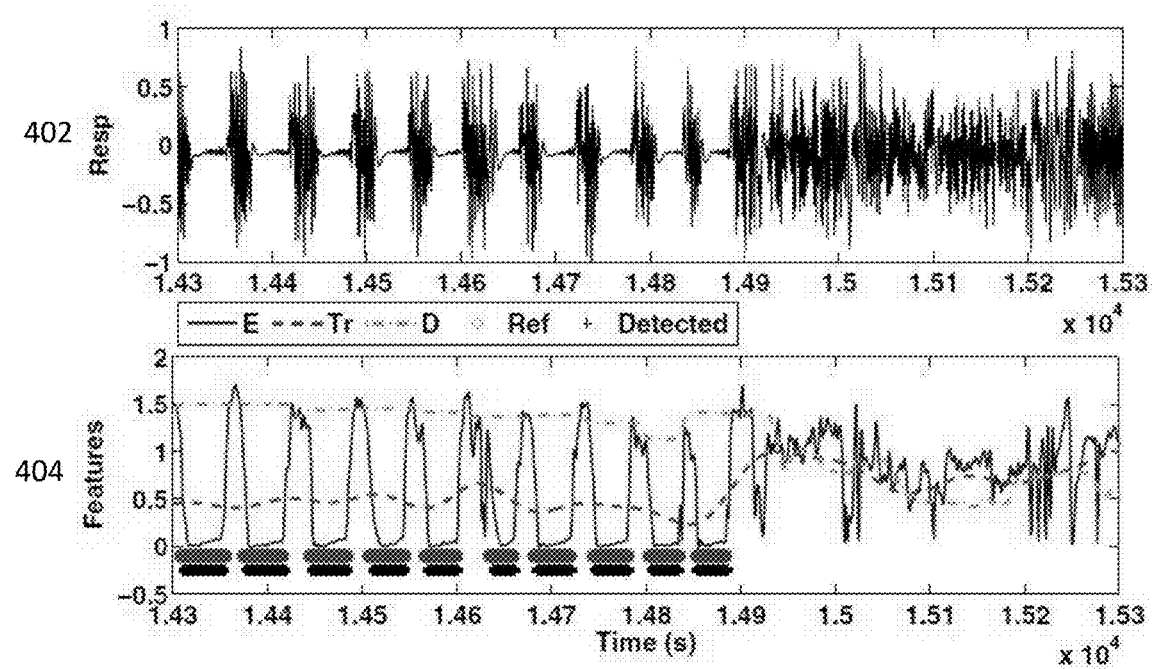
FIG. 4 illustrates a zoomed view diagram of the diagram depicting automated sleep apnea detection on an event-by-event basis using respiratory signals in accordance with an embodiment.

FIG. 4 illustrates a zoomed view diagram 400 of the diagram 300 depicting automated sleep apnea detection on an event-by-event basis using respiratory signals in accordance with an embodiment. The zoomed view diagram 400 includes a first graph 402 that depicts a zoomed in view of the respiratory signal and a second graph 404 that depicts a zoomed in view of the output of the apnea detection algorithm. In FIG. 4, there is good agreement of the locations and durations of apnea events compared to the reference annotations on a per-second basis. All ten apnea events are correctly detected in this example.

Figure 5:
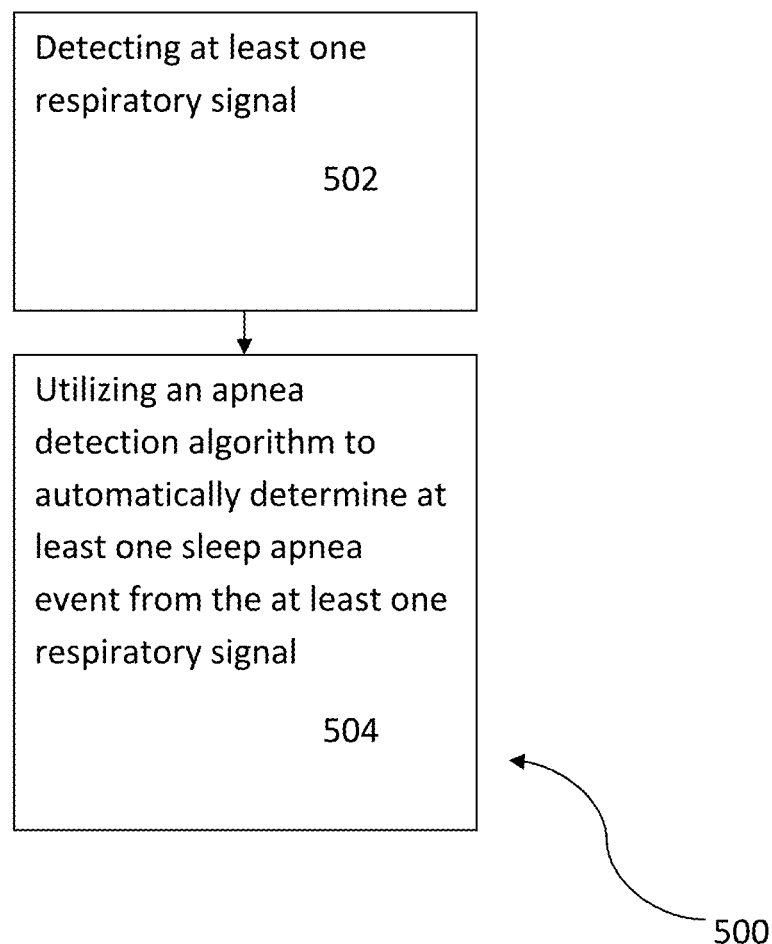
FIG. 5 illustrates a method for automated sleep apnea detection using respiratory signals in accordance with an embodiment.

FIG. 5 illustrates a method 500 for automated sleep apnea detection using respiratory signals in accordance with an embodiment. The method 500 includes detecting at least one respiratory signal, via step 502, and utilizing an apnea detection algorithm to automatically determine at least one sleep apnea event from the at least one respiratory signal, via step 504. In one embodiment, the at least one respiratory signal is any of a nasal airflow respiratory (NAR) signal, a respiratory inductive plethysomography (RIP) effort signal, and an electrocardiogram (ECG) derived respiratory signal. In one embodiment, the method 500 further includes pre-processing of the at least one detected respiratory signal using a plurality of low-pass filters that are $4^{th}$-order elliptic and reducing at least one false positive from the at least one determined candidate sleep apnea event.

In one embodiment, the utilizing step 504 further comprises extracting a plurality of features from the at least one respiratory signal, determining at least one candidate sleep apnea event using the plurality of features, and confirming a sleep apnea event using the at least one determined candidate sleep apnea event. In one embodiment, the plurality of features include any of a low-pass filtered envelope width, a trend mean of the low-pass filtered envelope width, and a statistical dispersion of the low-pass filtered envelope width that is a difference between $90^{th}$ and $10^{th}$ percentiles over a predetermined time period including but not limited to 120 seconds.

In one embodiment, the determining at least one candidate sleep apnea event step further comprises the satisfaction of two conditions: the first condition determines whether an instantaneous amplitude of a low-pass filtered envelope width of the at least one respiratory signal is less than an amplitude threshold times a trend mean of the low-pass filtered envelope width and the second condition determines whether the trend mean of the low-pass filtered envelope width is less than a variable times a statistical dispersion of the low-pass filtered envelope width. A counter is incremented if both aforementioned conditions are satisfied and if the counter is greater than a threshold, then the at least one candidate sleep apnea event is determined.

In one embodiment, the confirming step confirms whether a candidate sleep apnea event is actually a sleep apnea event. The confirming step further comprises the satisfaction of two conditions: the first condition determines whether a mean during an apnea event is less than a mean threshold times a mean during baseline and the second condition determines whether the mean during the apnea event is less than a variable times a mean dispersion metric. The apnea detection algorithm confirms the presence of at least one sleep apnea event if the mean during an apnea event is less than a mean threshold times a mean during baseline and the mean during the apnea event is less than a variable times a mean dispersion metric.

In another embodiment, a method for automated sleep apnea detection using respiratory signals includes respiratory signal detection, preprocessing of the detected respiratory signal, feature extraction from the preprocessed respiratory signal, candidate sleep apnea event detection, a rejection of potential false positive sleep apnea events, and a confirmation of sleep apnea events based on the candidate sleep apnea event detection.

As above described, a method and system in accordance with the present invention utilizes a wireless sensor device that detects and analyzes various respiratory signals of a user to automatically and continuously detect sleep apnea. By integrating machine learning based training datasets and an embedded apnea detection algorithm into the wireless sensor device, the testing datasets of the user that are continuously detected by the wireless sensor device are utilized to accurately detect sleep apnea and hypopnea related events. The wireless sensor device utilized the apnea detection algorithm to extra features from the respiratory signal, detect candidate sleep apnea events, and remove false positive events and confirm the detection of sleep apnea.

The apnea detection algorithm is fully automated, robust against noise (because all of the features are derived from the width of the envelope thereby enabling the apnea detection algorithm to be less sensitive to baseline wander of the NAR signal caused by motion artifacts) and takes less than 20 seconds on a typical computing machine (e.g. 2.7 GHz Intel Core i7 MacBook Pro Laptop) for the analysis of an overnight sleep testing recording of the user (via a PSG test or attached of the wireless sensor device to the user). The apnea detection algorithm also does not require any patient/user specific information. The low computational power requirement of the sleep apnea algorithm allows for real-time analysis as well as the cost-effective and battery efficient implementation into various portable devices (e.g. a wireless sensor device).

A method and system for automated sleep apnea detection using respiratory signals by a wireless sensor device have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A wireless sensor device for sleep apnea detection, the wireless sensor device comprising:
    a sensor to detect at least one respiratory signal;
    a processor coupled to the sensor; and
    a memory device coupled to the processor, wherein the memory device includes a detection algorithm and an application that, when executed by the processor, causes the processor to:
        extract a plurality of features from the at least one respiratory signal; and
        determine, using the detection algorithm, at least one sleep apnea event from the plurality of features,
    wherein determining the at least one sleep apnea event further causes the processor to:
        determine at least one candidate sleep apnea event using the plurality of features, and
        confirm the at least one sleep apnea event when:
            a mean during the at least one candidate sleep apnea event is less than a mean threshold times a mean during baseline, and
            the mean during the at least one candidate sleep apnea event is less than a variable time a mean dispersion metric.

2. The wireless sensor device of claim 1, wherein the at least one respiratory signal is any of a nasal airflow respiratory (NAR) signal, a respiratory inductive plethysomography (RIP) effort signal and electrocardiogram (ECG) derived respiratory signal.

3. The wireless sensor device of claim 1, wherein the application, when executed by the processor, further causes the processor to:
    preprocess of the at least one detected respiratory signal using a plurality of low-pass filters that are elliptic.

4. The wireless sensor device of claim 1, wherein the application, when executed by the processor, further causes the processor to:
    determine, using the detection algorithm, when the at least one candidate sleep apnea event is a false positive; and
    reject the at least one candidate sleep apnea event when the at least one candidate sleep apnea event is false positive, wherein the at least one candidate sleep apnea event is determined to be false positive when at least one of the following conditions is true:
        the mean during the at least one candidate sleep apnea event is not less than the mean threshold times the mean during baseline, and
        the mean during the at least one candidate sleep apnea event is not less than the variable times the mean dispersion metric.

5. The wireless sensor device of claim 1, wherein the plurality of features include any of a low-pass filtered envelope width, a trend mean of the low-pass filtered envelope width, and a statistical dispersion of the low-pass filtered envelope width.

6. The wireless sensor device of claim 5, wherein the statistical dispersion of the low-pass filtered envelope width is a difference between $90^{th}$ and $10^{th}$ percentiles over a predetermined time period.

7. The wireless sensor device of claim 1, wherein to determine the at least one candidate sleep apnea event further comprises to:
- determine whether an instantaneous amplitude of a low-pass filtered envelope width of the at least one respiratory signal is less than an amplitude threshold times a trend mean of the low-pass filtered envelope width; and
- determine whether the trend mean of the low-pass filtered envelope width is less than a variable times a statistical dispersion of the low-pass filtered envelope width.

8. The wireless sensor device of claim 7, wherein determining the at least one candidate sleep apnea event further comprises:
- incrementing a counter if the instantaneous amplitude of the low-pass filtered envelope width is less than the amplitude threshold times the trend mean, and the trend mean of the low-pass filtered envelope width is less than the variable times the statistical dispersion of the low-pass filtered envelope width; and
- comparing the counter to a threshold and determining the at least one candidate sleep apnea event based on result of the comparing.

* * * * *